(12) United States Patent
Klaue

(10) Patent No.: US 9,375,241 B2
(45) Date of Patent: Jun. 28, 2016

(54) BONE NAIL FOR THE HEEL

(75) Inventor: Kaj Klaue, Savosa (CH)

(73) Assignee: Biedermann Technologies GmbH & Co. KG, Donaueschingen (DE)

( * ) Notice: Subject to any disclaimer, the term of this patent is extended or adjusted under 35 U.S.C. 154(b) by 472 days.

(21) Appl. No.: 12/734,833

(22) PCT Filed: Nov. 10, 2008

(86) PCT No.: PCT/CH2008/000474
§ 371 (c)(1),
(2), (4) Date: Jul. 26, 2010

(87) PCT Pub. No.: WO2009/067831
PCT Pub. Date: Jun. 4, 2009

(65) Prior Publication Data
US 2010/0305623 A1 Dec. 2, 2010

(30) Foreign Application Priority Data

Nov. 26, 2007 (CH) .................................. 1825/07
Dec. 27, 2007 (CH) .................................. 2010/07

(51) Int. Cl.
*A61B 17/86* (2006.01)
*A61B 17/72* (2006.01)
*A61B 17/17* (2006.01)

(52) U.S. Cl.
CPC ............. *A61B 17/72* (2013.01); *A61B 17/7283* (2013.01); *A61B 17/1717* (2013.01);
(Continued)

(58) Field of Classification Search
USPC ......... 606/60, 62–68, 72, 167, 297, 300–321, 606/329; 411/487; 623/21.14–21.19
See application file for complete search history.

(56) References Cited

U.S. PATENT DOCUMENTS

| 1,630,239 A | 5/1927 | Binkley et al. |
| 4,541,423 A | 9/1985 | Barber |

(Continued)

FOREIGN PATENT DOCUMENTS

| CA | 2 608 286 | 11/2006 | |
| CH | WO 2007/053960 | * 5/2007 | ............. A61B 17/17 |

(Continued)

OTHER PUBLICATIONS

International Search Report issued Sep. 2, 2010 for Application No. PCT/IB2010/001089, 15 sheets.

(Continued)

*Primary Examiner* — Christian Sevilla
*Assistant Examiner* — Eric S Gibson
(74) *Attorney, Agent, or Firm* — Lewis Roca Rothgerber Christie LLP

(57) ABSTRACT

The bone nail is intended for the heel. It comprises a front part (15) that is intended to be inserted in the bone and is provided with a tip (17) and it also comprises a rear part (16) having an end (18). The rear part (16) is rigid at a length of at least 120 mm, starting from the end (18). The bone nail is cured in a plane and the curvature for each infinitesimal section of the bone nail has a curvature radius that is at least 130 mm. The key advantages that can be achieved with the bone nail according to the invention and thanks to the surgical technique that becomes possible with it are the possibility to adjust the heel with high precision relative to the lower leg and knee axis, the avoidance of the risk of an injury to the plantar nerves, and a less invasive implant compared to the known surgical techniques using other nails.

26 Claims, 6 Drawing Sheets

Figure 1:
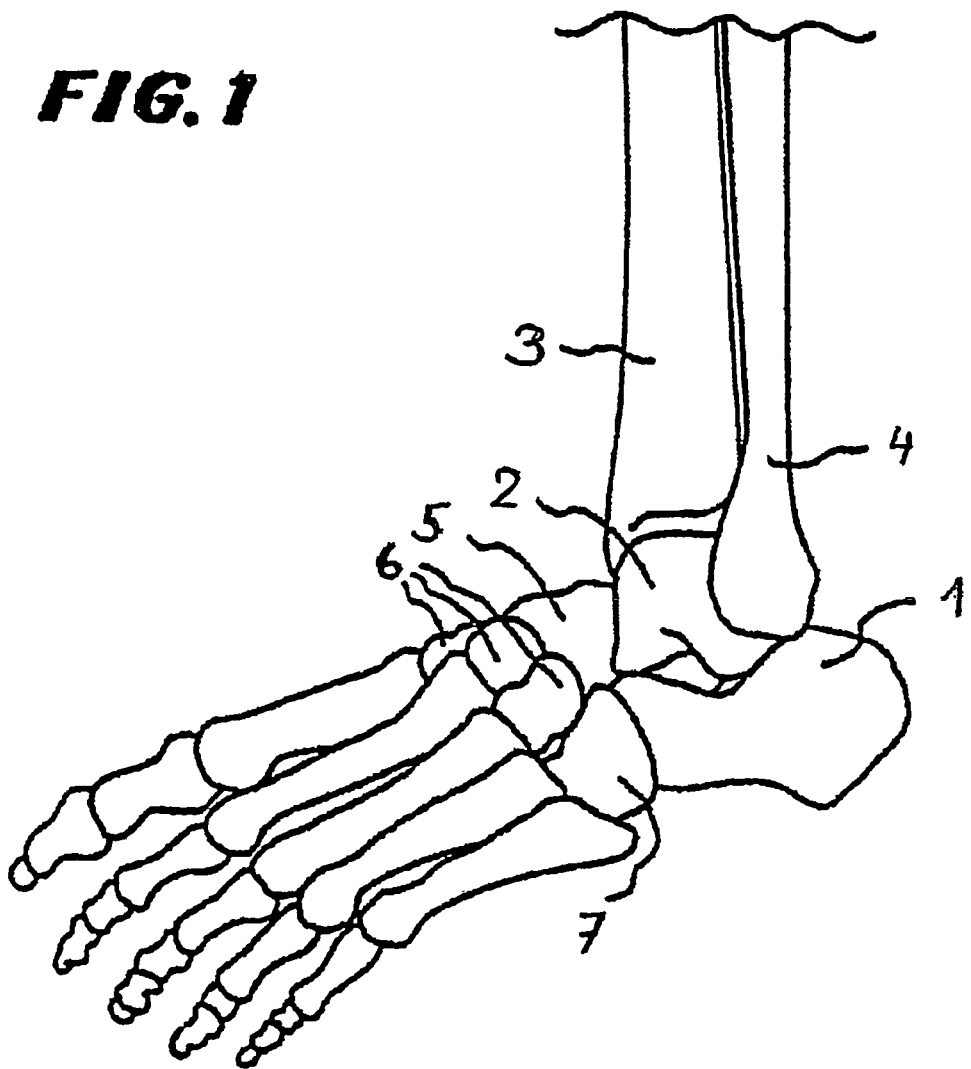

(52) U.S. Cl.
CPC ......... *A61B17/7208* (2013.01); *A61B 17/7233* (2013.01); *A61B 17/7291* (2013.01); *A61B 2017/1775* (2013.01)

(56) References Cited

U.S. PATENT DOCUMENTS

| | | | |
|---|---|---|---|
| 4,877,019 A * | 10/1989 | Vives | 606/64 |
| 5,035,697 A | 7/1991 | Frigg | |
| 5,041,115 A * | 8/1991 | Frigg et al. | 606/62 |
| 5,053,035 A * | 10/1991 | McLaren | 606/67 |
| 5,312,406 A * | 5/1994 | Brumfield | 606/64 |
| 5,531,748 A | 7/1996 | de la Caffiniere | |
| 5,624,447 A | 4/1997 | Myers | |
| 5,735,899 A | 4/1998 | Schwartz et al. | |
| 5,855,579 A * | 1/1999 | James et al. | 606/62 |
| 5,871,486 A | 2/1999 | Huebner et al. | |
| 5,968,048 A | 10/1999 | Harder | |
| 6,074,392 A * | 6/2000 | Durham | 606/67 |
| 6,102,914 A | 8/2000 | Bulstra et al. | |
| 6,461,360 B1 * | 10/2002 | Adam | 606/67 |
| 6,579,293 B1 | 6/2003 | Chandran | |
| 6,629,976 B1 * | 10/2003 | Gnos et al. | 606/62 |
| 6,702,816 B2 * | 3/2004 | Buhler | 606/62 |
| 6,709,436 B1 * | 3/2004 | Hover et al. | 606/62 |
| 7,963,967 B1 | 6/2011 | Woods | |
| 8,066,706 B2 * | 11/2011 | Schlienger et al. | 606/64 |
| 2004/0049192 A1 | 3/2004 | Shimizu | |
| 2005/0267481 A1 | 12/2005 | Carl et al. | |
| 2005/0277936 A1 * | 12/2005 | Siravo et al. | 606/62 |
| 2006/0129153 A1 | 6/2006 | Klaue et al. | |
| 2006/0200141 A1 * | 9/2006 | Janna et al. | 606/62 |
| 2006/0241605 A1 * | 10/2006 | Schlienger et al. | 606/62 |
| 2007/0225721 A1 | 9/2007 | Thelen et al. | |
| 2007/0276385 A1 * | 11/2007 | Schlienger et al. | 606/72 |
| 2007/0288017 A1 * | 12/2007 | Kaup | 606/62 |
| 2008/0140078 A1 | 6/2008 | Nelson et al. | |
| 2008/0262496 A1 | 10/2008 | Schlienger et al. | |
| 2010/0292722 A1 | 11/2010 | Klaue | |
| 2010/0305623 A1 | 12/2010 | Klaue | |
| 2011/0087228 A1 | 4/2011 | Ferrante et al. | |
| 2012/0143192 A1 | 6/2012 | Watanabe et al. | |

FOREIGN PATENT DOCUMENTS

| | | |
|---|---|---|
| DE | 133162 | 10/1901 |
| DE | 76 07 981 U1 | 11/1977 |
| JP | 2005-504573 A | 2/2005 |
| JP | 2005-507726 A | 3/2005 |
| JP | 2006-510445 A | 3/2006 |
| JP | 2011-505180 A | 2/2011 |
| WO | WO 90/12550 | 11/1990 |
| WO | WO 90/12550 A | 11/1990 |
| WO | WO 03/017822 A | 3/2003 |
| WO | WO 03/017822 A2 | 3/2003 |
| WO | WO 03/028533 A2 | 4/2003 |
| WO | WO 03/039330 A2 | 5/2003 |
| WO | WO 2004/056285 A1 | 7/2004 |
| WO | WO 2004/089255 A1 | 10/2004 |
| WO | WO 2006/119659 A | 11/2006 |
| WO | WO 2006/119659 A1 | 11/2006 |
| WO | WO 2007/053960 * | 5/2007 |
| WO | WO 2007/053960 A | 5/2007 |
| WO | WO 2007/053960 A1 | 5/2007 |
| WO | WO 2007/120539 A | 10/2007 |
| WO | WO 2007/120539 A2 | 10/2007 |
| WO | WO 2008/099176 A1 | 8/2008 |
| WO | WO 2009/067831 A1 | 6/2009 |

OTHER PUBLICATIONS

International Search Report, dated Jan. 8, 2009, corresponding to PCT/CH2008/000474, 8 pages.
Final Office action for U.S. Appl. No. 12/781,168, dated Jan. 22, 2013, 12 pages.
Office action for U.S. Appl. No. 14/080,778, dated Jul. 14, 2014, 13 pages.
Final Rejection for U.S. Appl. No. 14/080,778, dated May 1, 2015, 22 pages.
Office action for U.S. Appl. No. 12/781,168, dated Apr. 27, 2012, 11 pages.
Final Rejection for U.S. Appl. No. 12/781,168, dated Jan. 22, 2013, 12 pages.
Office action for U.S. Appl. No. 12/781,168, dated Sep. 4, 2014, 21 pages.
Final Rejection for U.S. Appl. No. 12/781,168, dated May 4, 2015, 23 pages.
Office action for U.S. Appl. No. 14/080,778, dated Nov. 4, 2015, 26 pages.

* cited by examiner

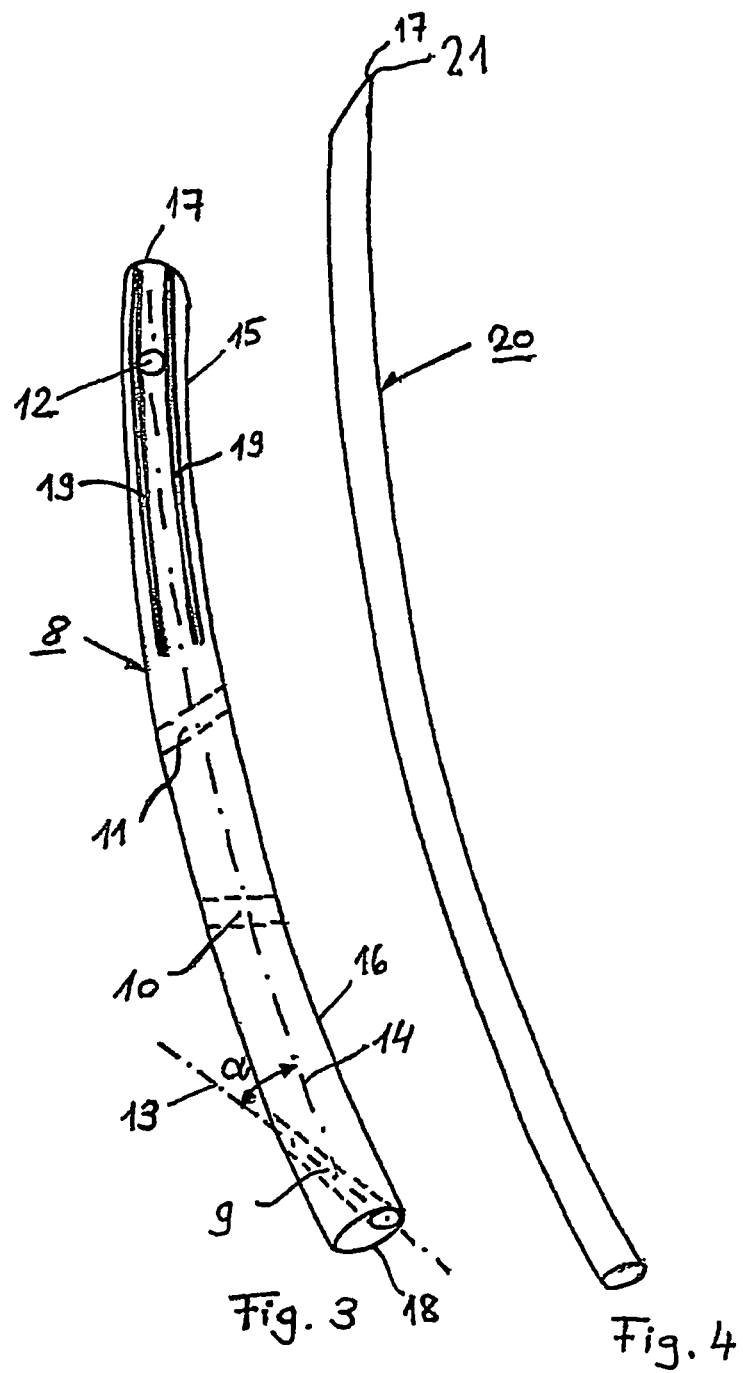

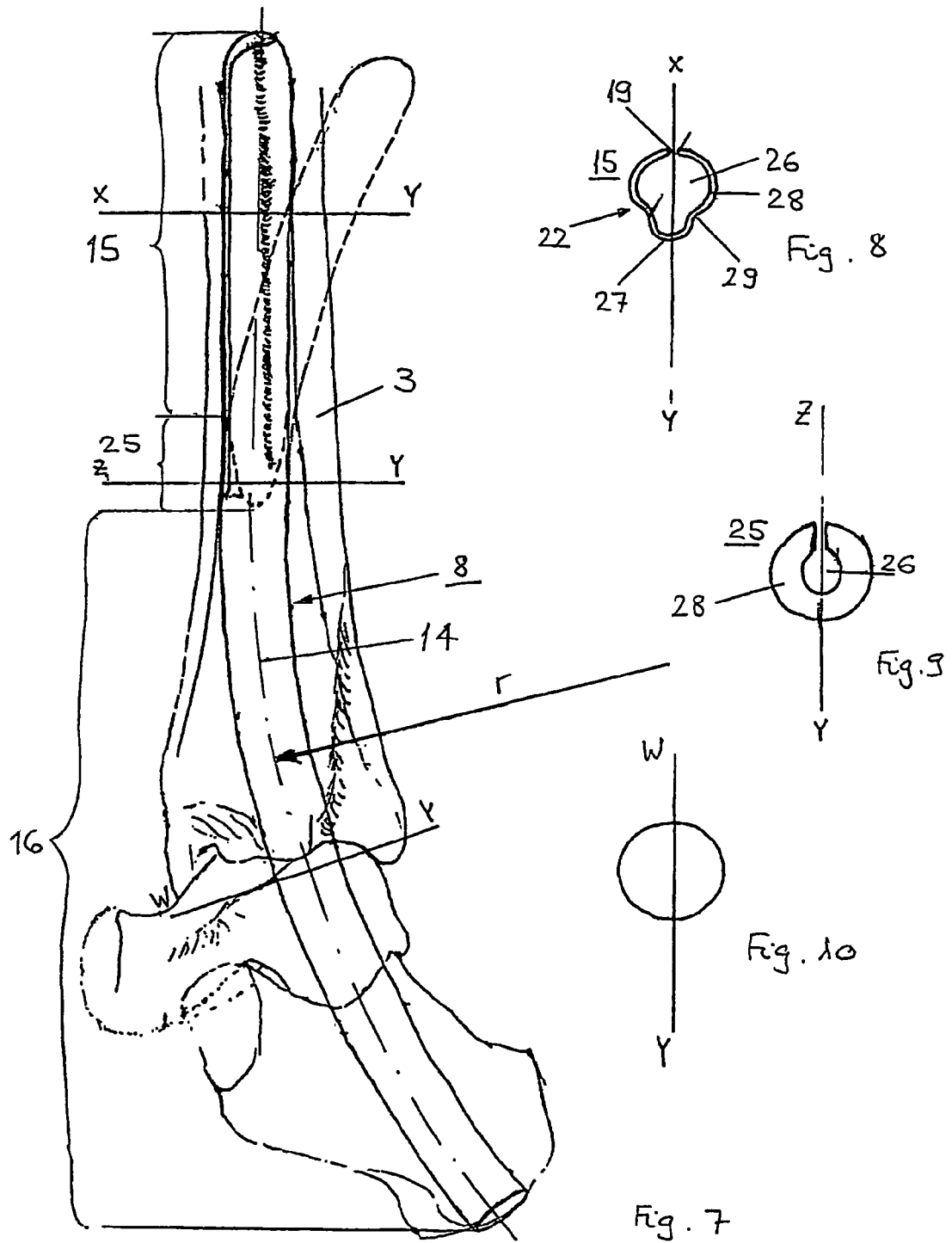

BONE NAIL FOR THE HEEL

CROSS-REFERENCE TO REATED APPICATION

This application is a National Phase Patent Application and claims the priority of International application No. PCT/CH2008/000474, filed on Nov. 10, 2008, which claims priority of Swiss Patent Application Number 1825/07, filed on Nov. 26, 2007 and Swiss Patent Application Number 2010/07, filed on Dec. 27, 2007.

The invention relates to a bone nail for the heel according to the preamble of claim 1, and to an osteosynthesis-kit according to the preamble of claim 16, and to an application of the bone nail to tibio-calcaneal arthrodesis according to claim 17.

Marrow nails which reveal a curvature in a portion thereof have been known for a long time. As an example so-called ENDER-nails may be cited in this regard. However, these known nails are formed elastically and flexibly due to their purpose of application, such that these nails already bend upon small loads. Due to the flexibility of these known nails it is even unimportant that the intermediate part is rectilinear and comprises no curvature. These known ENDER-nails further stand out due to their relative length and tenuity. The ratio between the diameter of the nail and the length of the nail lies in the case of ENDER in the range from 1:60 to 1:110. An application in the field of heels is ruled out for these reasons.

Further, tibia-nails are known which are partially curved, however, the radii of curvature of these known nails are comparatively small, namely in the range of 100 and 120 mm, such that these nails do not come into consideration for an application in the field of heels.

Herein, the invention tries to find a remedy. An object underlies the invention to provide a bone nail for the heel, which due to its shape and material properties can be inserted through the calcaneus and talus up into the marrow space of the tibia. In medical terms it is dealt with so-called tibio-calcaneal arthrodesis, which is sometimes also called "double anthrodesis".

The invention solves the object by a bone nail, which comprise the features according to claim 1, by an osteosynthesis-kit, which comprises the features of claim 16, and by a method of use of the bone nail according to claim 17.

The substantial advantages, which may be achieved by the bone nail according to the invention and by the surgical technique that becomes possible thereby, are as follows:
- possibility of the high-precision orientation of the rear foot in relation to the lower leg and knee axis;
- avoidance of the risk of an injury of the plantar-nerves; as well as
- a less invasive implantation as compared with other techniques, which have to be applied with nails according to prior art.

Due to the bone nail according to the invention there can now even be treated novel indications, such as for example the treatment of:
- diabetical feet;
- painful arthroses of the upper and lower subtalar joint;
- necrosis of the Talus; and
- patients having circulatory disorder.

In a specific embodiment the bone nail has a radius of curvature of 240 mm at maximum, preferably 210 mm at maximum. Typically the radius of curvature amounts to about 190 mm.

Purposefully, the radius of curvature does not vary along the entire length of the bone nail by more than 1% and is preferably constant. Alternatively, the radius of curvature may, however, also increase preferably steadily in the front part in a direction towards the tip of the bone nail.

In a specific embodiment the bone nail is formed stiffly over its entire length. This arrangement is most appropriate for the embodiment as a milling cutter guiding mandrel.

In another embodiment the front part is formed less stiffly than the rear part and preferably is plastically deformable. This arrangement is most appropriate for the embodiment as an implant.

In the front part of the bone nail longitudinal channels may be provided, such that the front part includes a cross-section being smaller than the rear part. Due to the weakening of the cross-section, a flexibilization of the front part is achieved as opposed to the stiff rear part, a fact which offers advantages with regard to the embodiment as an implant. The marrow nail may be formed with tubular shape also in its tip half, preferably having a wall thickness of 0.5 mm.

The front part purposefully includes not more than 50% of the stiffness of the rear part.

The front part as well as the rear part of the bone nail can make up between 30 and 70% of the entire length of the bone nail.

In one embodiment the bone nail is formed as an implant having a diameter $D_I$ ranging from 9 to 13 mm. In another embodiment the bone nail is formed as a milling cutter guiding mandrel having a diameter $D_D$ in the range from 3 to 7 mm.

The bone nail is preferably flexurally rigid and may for example be formed from hardened steel. The bending stiffness B is according to Wikipedia calculated according to the formula: $B = E \times I$, wherein I is the $2^{nd}$ order moment of area in $mm^4$, and E is the E-module in $N/mm^2$. I depends on the bending axis chosen; however, in case of rotational symmetric cross-sectional surfaces I plays no role.

The radius R of curvature of the bone nail lies purposefully in the range from 140 to 240 mm, preferably from 150 to 210 mm. These ranges for the radius of curvature allow for an optimal placement of the bone bore via the milling cutter guiding mandrel and—after completion of the milling process—an optimal insertion of the implant into the three respective bones: calcaneus, talus and tibia. Advantageously, the radius R of curvature is constant over the entire length of the bone nail. Since the bone nail—in its arrangement as a milling cutter guiding mandrel as well as an implant—is stiff and may thus not be bent, the constant curvature is advantageous, in order to be able to drive the bone nail into the respective bone with least possible efforts.

The bone nail is appropriately curved over its entire length, most preferably in a steady manner. This arrangement leads to an easiest possible insertion of the bone nail: a bone nail having a rectilinear section (besides curved sections) would impede the insertion due to an abutment of the bone nail at the wall of the bore.

In a particular embodiment the bone nail formed as an implant includes a length $L_I$ less than 160 mm, preferably less than 150 mm. With this length the implant reaches up to a region of the tibia, where due to the width of the marrow channel some amount of balancing may take place; at a larger nail length the tip of the bone nail would arrive in a narrower region of the Tibia marrow channel, which would impede further insertion. The length $L_I$ is, however purposefully larger than 125 mm, preferably larger than 130 mm.

In a specific embodiment the bone nail formed as an implant extends over a circular arc ranging from 38° to 70°, preferably from 48° to 55°.

In another embodiment the bone nail formed as a milling cutter guiding mandrel includes a length $L_D$ in the range from 200 to 260 mm.

The bone nail formed as an implant purposefully has a ratio $L_I/D_I$ between its length $L_I$ and its diameter $D_I$, which is less than 16, preferably less than 14. The bone nail formed as a milling cutter guiding mandrel purposefully has a ratio $L_D/D_D$ between its length $L_D$ and its diameter $D_D$ in the range from 30 to 90.

In a particular embodiment the bone nail has at least one transverse bore for receiving a locking screw, wherein the length axis of the transverse bore preferably lies within the plane of curvature of the bone nail. The transverse bore may, for example, lie in the head region of the bone nail, and its longitudinal axis may include an angle α with the longitudinal axis of the bone nail of preferably 10° to 20°.

In a particular embodiment the bone nail formed as a milling cutter guiding mandrel comprises a sharp tip, preferably in the shape of a tip of a chisel. The tip of the chisel is preferably chamfered only on one side, preferably on the outside of the curvature of the bone nail.

In a further embodiment the radius of curvature of the bone nail or of the bone nail formed as the milling cutter guiding mandrel amounts to at least 190 mm, preferably at least 200 mm.

In another embodiment the bone nail comprises at least in its front part a longitudinal slit.

In a further embodiment the bone nail comprises at least in its front part a shamrock-shaped cross-section.

In still another embodiment the rear part of the bone nail is formed stiffly.

In another embodiment the bone nail comprises an intermediate part between the front part and the rear part, wherein the stiffness of the intermediate part increases towards the rear part.

In another embodiment the bone nail comprises at least in its front part a cavity which is parallel to the longitudinal axis.

At least one bone nail formed as an implant in conjunction with at least one bone nail formed as a milling cutter guiding mandrel can be combined to an osteosynthesis-kit, wherein the radii of curvature of the implant and of the milling cutter guiding mandrel must be of the same size. The length $L_D$ of the milling cutter guiding mandrel in such a kit is preferably 80 to 120 mm, preferably 90 to 110 mm longer than the length $L_I$ of the implant.

The invention and further aspects of the invention will be explained in more detail in what follows using the partly schematical illustrations of multiple embodiments.

Figure 2:
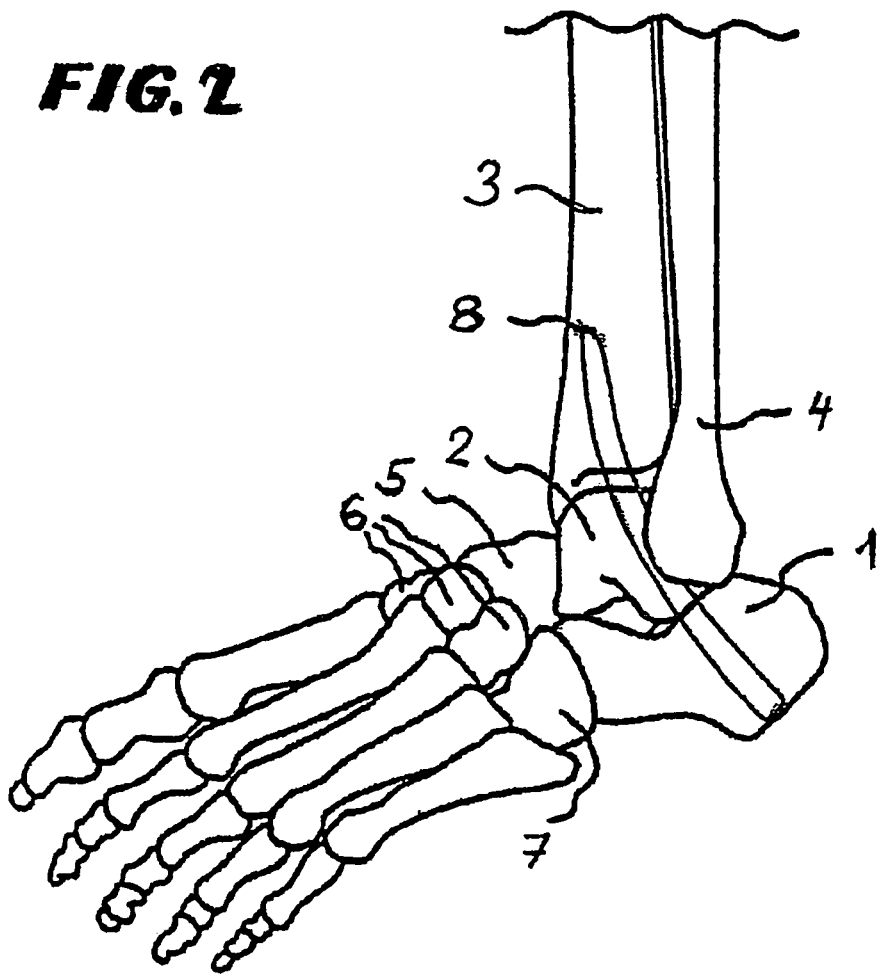
Figure 5:
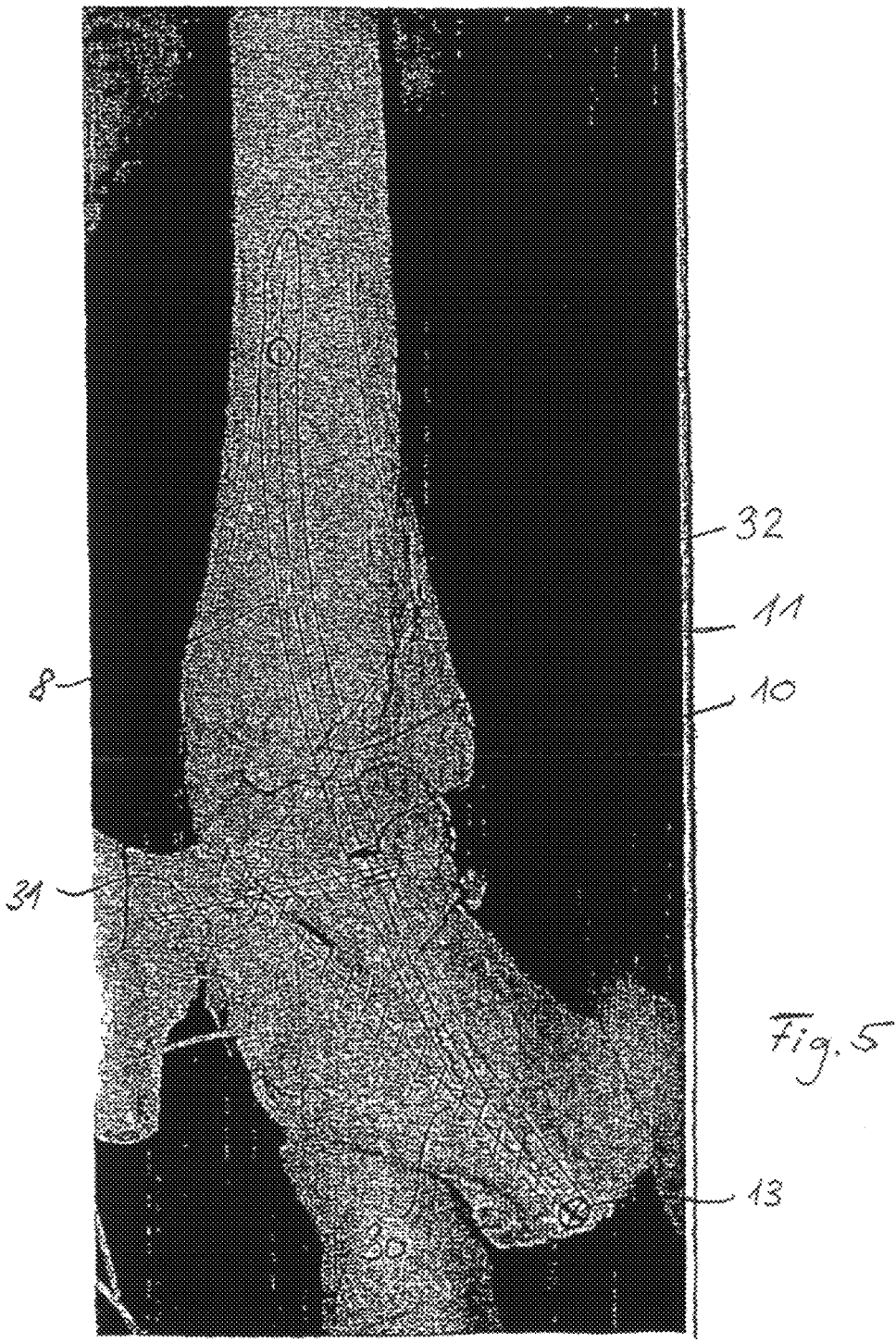
Figure 6:

It is shown in:

FIG. 1 a schematical oblique view of the lower leg and foot bones;

FIG. 2 an embodiment of the bone nail according to the invention implanted into the bone;

FIG. 3 a schematical view of the bone nail according to the invention according to FIG. 2 in its arrangement as an implant;

FIG. 4 a schematical view of the bone nail according to the invention in its arrangement as a milling cutter guiding mandrel;

FIG. 5 the bone nail implanted into the bone according to FIGS. 2 and 3 taken from an oblique front side and its locking by three locking screws;

FIG. 6 the positioning of the implanted bone nail according to FIGS. 2 and 3 when seen from plantar;

FIG. 7 a schematical view from antero-lateral of a further embodiment of the bone nail according to the invention implanted into the bone;

FIG. 8 a cross-section at line X-Y in FIG. 7;

FIG. 9 a cross-section at line Z-Y in FIG. 7; and

FIG. 10 a cross-section at line W-Y in FIG. 7.

FIG. 1 shows the lower leg in a position in which it is rotated towards an inner direction by about 45°. Those bones are illustrated, which are relevant for the application of the bone nail according to the invention. Primarily concerned are the calcaneus 1, the talus 2 and the tibia 3. The further illustrated fibula 4, os naviculare 5, ossa cuneiformia 6 and os cuboideum 7 are only drawn for the purpose of completeness.

In FIG. 2 the bone nail according to the invention formed as an implant 8 has been drawn, which has been implanted through the Calcaneus 1 and the Talus 2 up into the lower part of the Tibia 3. As illustrated in FIG. 3, the implant 8 is steadily curved within a plane having the radius R of curvature of typically 190 mm. The curvature extends over the entire length $L_I$ of the implant 8, which typically amounts to 140 mm. Its diameter $D_I$ typically amounts to 11 mm. The ratio $L_I/D_I$ between the length $L_I$ and diameter $D_I$ of the implant 8 typically amounts to 12.7.

The implant 8 includes a number of transverse bores 9, 10, 11, 12, into which locking screws 30 can be inserted. Three of the transverse bores 9, 11, 12 lie in the same plane within which the implant 8 is curved. A fourth transverse bore 12 lies at a proximal end of the implant 8 and extends orthogonally to the mentioned curvature plane.

The longitudinal axis 13 of the transverse bore 9 positioned at the distal end of the implant 8 includes an angle α of 15° with the longitudinal axis 14 of the implant 8.

The implant 8 is composed of a stiff material—in particular with regard to bending—and is for example composed of one of the known implant steels, which are preferably hardened, in order to further increase the bending stiffness of the implant 8.

In order to be able to insert the implant 8 into the bone, it is preferable—depending on the bone quality—to drill up the respective bones 1, 2, 3 in advance. This is carried out using the bone nail illustrated in FIG. 4 in an embodiment as a milling cutter guiding mandrel 20 for a bone milling cutter. The milling cutter guiding mandrel 20 must necessarily include the same curvature—lying within a plane—as the bone nail formed as an implant 8 and must also be composed of a stiff material. It is on the contrary formed with a larger length—typically longer by about 100 mm—than the bone nail formed as an implant 8 and is necessarily formed thinner than the latter; typically its diameter amounts to about 5 mm.

The milling cutter guiding mandrel 20 includes a sharply formed tip 17 in the form of a chisel tip 21, in order that it can be easily driven into the calcaneus 1. The chisel tip 21 is chamfered only on one side, namely on the outer side of the curvature of the milling cutter guiding mandrel 20.

In FIG. 5 the foot is rotated towards an inner direction together with the lower leg by about 45°. The implant 8 is illustrated in its finally implanted position. A first locking screw 30 within the transverse bore 9 secures the implant 8 in the calcaneus 1 and in the talus 2. A second locking screw 31 in the transverse bore 10 locks the implant 8 in the talus 2. A third locking screw 32 in the transverse bore 11 locks the implant 8 in the tibia 3 and in the talus 2. Hence, the three bones tibia 3, talus 2 and calcaneus 1 are stiffened together and more specifically—what is important—in an anatomically correct orientation.

FIG. 6 shows the left rear foot (skeleton) with the positioning of the entrance location of the bone nail provided as an implant 8 according to the invention, and with its course through the bone in a plantar view.

In FIGS. 7-10 a further embodiment of the implant 8 in the form of a bone nail is illustrated, which deviates from the embodiments shown according to FIGS. 2-6 merely in that the bone nail:

a) comprises in its front part 15 a shamrock-shaped cross-section 22 (FIG. 8), a cavity 26 parallel to its longitudinal axis 14 and a longitudinal slit 19 parallel to the longitudinal axis 14; and b) comprises an intermediate part 25 between its front part 15 and its rear part 16, the intermediate part 25 being formed as a transitional region between the front part 15 with low stiffness and the rear part 16 with high stiffness, such that the stiffness of the bone nail increases towards the rear part 16 continuously.

Due to the cavity 26 the bone nail obtains in the front part 15 a thin-walled cross-section 22 including a peripheral wall 28 having a small wall thickness, the wall 28 further being separated by the longitudinal slit 19 which is parallel to the longitudinal axis 14. The shamrock-shape in the cross-section 22 results from the wall 28 being formed with two indentations 29 extending in the front part 15 parallel to the longitudinal axis 14. The two indentations 29 are arranged on the periphery of the bone nail, such that a convex bend 27 of the wall 28 is formed diametrally opposing the longitudinal slit 19 and extending likewise parallel to the longitudinal axis. In the intermediate part 25 the stiffness of the front part 15 increases towards the rear part 16 due to a growing wall thickness of the wall 28 towards the rear part 16. This growing wall thickness is achieved on the one side by a continuous narrowing of the cavity 26 and on the other side by a continuous decrease of the radially measured depth of the indentations 29 in the wall 28 towards the rear part 16, such that a continuous transition from the shamrock-shaped cross-section 22 in the front part 15 is formed towards the circular cross-section 24 in the rear part 16. Prior to the implantation, the intermediate part 25 and the front part 15 have a curved shape (illustrated as dashed) including the same radius r of curvature as the rear part 16. Due to the reduced stiffness of the intermediate part 25 and in particular of the front part 15 these may deform during the insertion into the tibia 3, such that the front part 15 may comprise a substantially larger radius of curvature after the implantation or may even have a rectilinear form.

In the following the general surgical method is defined:
1. Removal of cartilage from the joints and mobilization of the three bones: tibia 3; talus 2 and calcaneus 1.
2. Adjustment of the desired position of the above-mentioned three bones with regard to angular orientation and shift.
3. Fixation of the above-mentioned three bones with regard to their relative adjusted position by means of the bone nail formed as the implant 8; and
4. Optional locking of the implant 8 using the locking screws 30.

In the following a more detailed surgical technique for the bone nail formed as an implant 8 is described:
a) Bring patient into dorsal, ventral or lateral position;
b) By virtue of a targeted, limited, front-, lateral- or postero-lateral aditus, both joints (upper and subtalar) are accessed, whereby remaining cartilage is removed;
c) Tibia 3, talus 2 and calcaneus 1 shall be freely movable in order to achieve the desired re-orientation (alignment);
d) The targeted position is fixed using percutaneously inserted, rigid Kirschner wires 19 (3 mm diameter);
e) Establish aditus of about 2-3 cm length at the lateral heel;
f) Locate margin of postero-lateral Calcaneus (tuber calcanei);
g) Drill-up the corticalis (thin) with a drill of 5-7 mm;
h) Insert into the calcaneus 1 an arcuate bone nail according to the invention which is grinded on a single side at its tip and which is provided in its embodiment as a milling cutter guiding mandrel 20 (diameter 6 mm) in an oblique plane with regard to the rear foot (about 45° from postero-lateral, as seen from the sagittal or frontal plane) [see FIG. 6];
i) Traverse of the calcaneus 1 and the talus 2 on the level of the posterior subtalar joint facet;
j) Proximal traverse of the talus 2 at the level of the mandrel;
k) Threading of the metaphysis of the tibia 3 until the milling cutter guiding mandrel 20 abuts on the postero-lateral corticalis;
l) The milling cutter (diameter 11 mm) is threaded onto the milling cutter guiding mandrel 20 and the path for the bone nail formed as an implant 8 is milled;
m) Pull-out of the milling cutter and the milling cutter guiding mandrel 20;
n) Insertion of the implant 8 with an optional target handle, which contains bores for the locking screws 30;
o) Percutaneous insertion of the optional locking screws 30 (for the tibia 3, the talus 2 and the calcaneus 21); and
p) Application of the skin suture.

The invention claimed is:

1. A bone nail for a heel comprising:
a front part dimensioned for insertion into a calcaneus and having a tip;
a rear part having an end; wherein
the rear part has a length of at least 120 mm starting from the end;
the bone nail is curved within a plane;
the curvature for each infinitesimal section of the bone nail on a length of at least 120 mm includes a radius of curvature which lies in a range from 130 mm to 240 mm; and
wherein the rear part has a constant radius of curvature over its entire length.

2. The bone nail according to claim 1, wherein the radius of curvature amounts to not more than 210 mm.

3. The bone nail according to claim 1, wherein the radius of curvature increases steadily in the front part towards the tip.

4. The bone nail according to claim 1, wherein the front part is less stiff than the rear part and is formed being plastically deformable.

5. The bone nail according to claim 1, wherein said bone nail is formed as an implant and includes at least one transverse bore for receiving a locking screw, wherein a longitudinal axis of the transverse bore lies within a radius of curvature of the bone nail.

6. The bone nail according to claim 1, wherein the radius of curvature amounts to at least 190 mm.

7. The bone nail according to claim 1, wherein said bone nail comprises at least in its front part a longitudinal slit extending to a distal end of the tip.

8. The bone nail according to claim 1, wherein said bone nail comprises at least in the front part a shamrock-shaped cross-section.

9. The bone nail according to claim 1, wherein the bone nail comprises between the front part and the rear part an intermediate part with a stiffness less than a stiffness of the rear part and wherein the stiffness of the intermediate part comprises a continuous transition to the stiffness of the rear part.

10. The bone nail according to claim 1, wherein the bone nail comprises at least in the front part a cavity parallel to a longitudinal axis.

11. A method of use of a bone nail according to claim 1, for tibio-calcaneal arthrodesis into a patient comprising a tibia, a talus and a calcaneus bone, the method comprising fixing the tibia, talus and the calcaneus bones with respect to each other by means of the bone nail.

12. The bone nail according to claim 1, wherein the bone nail is formed as an implant and a ratio $L_I/D_I$ between a length $L_I$ of the bone nail and a diameter $D_I$ of the bone nail is less than 16.

13. The bone nail according to claim 1, wherein the entire bone nail is curved within said plane.

14. The bone nail according to claim 13, wherein the radius of curvature for the entire bone nail is constant.

15. The bone nail according to claim 13, wherein the radius of curvature for the entire bone nail does not vary by more than 1%.

16. A bone nail for a heel including:
- a front part dimensioned for insertion into a calcaneus and having a tip;
- a rear part having an end; wherein
- the rear part has a length of at least 120 mm starting from the end;
- the bone nail is curved within a plane;
- the curvature for each infinitesimal section of the bone nail includes a radius of curvature which amounts to at least 130 mm; and
- the front part is less stiff than the rear part such that the front part is plastically deformable; and
- the bone nail has a diameter ranging from 9 mm to 13 mm.

17. The bone nail according to claim 16, wherein the radius of curvature increases steadily in the front part towards the tip.

18. The bone nail according to claim 16, wherein the entire bone nail is curved within said plane, and wherein the radius of curvature for the entire bone nail is constant.

19. A bone nail for a heel comprising:
- a front part dimensioned for insertion into a calcaneus and having a tip;
- a rear part having an end; wherein
- the bone nail is curved within a plane;
- the curvature for each infinitesimal section of the bone nail has a radius of curvature which lies in a range from 130 mm to 240 mm; and
- wherein the bone nail is formed as an implant and a ratio $L_I/D_I$ between a length $L_I$ of the bone nail and a diameter $D_I$ of the bone nail is less than 16.

20. The bone nail according to claim 19, wherein the entire bone nail is curved within said plane, and wherein the radius of curvature for the entire bone nail is constant.

21. A bone nail for a heel comprising:
- a front part configured for insertion into a bone and having a tip;
- a rear part having an end; wherein
- the rear part has a length of at least 120 mm starting from the end;
- the bone nail is curved along a plane;
- the curvature for each infinitesimal section of the bone nail on a length of at least 120mm includes a radius of curvature which lies in a range from 130 mm to 240 mm; and
- wherein the bone nail has the same radius of curvature along its entire length along said plane, and wherein the bone nail comprises between the front part and the rear part an intermediate part with a stiffness less than a stiffness of the rear part and wherein the stiffness of the intermediate Dart comprises a continuous transition to the stiffness of the rear part.

22. The bone nail according to claim 21, wherein the radius of curvature amounts to not more than 210 mm.

23. The bone nail according to claim 21, wherein the radius of curvature amounts to at least 190 mm.

24. A method of use of a bone nail for tibio-calcaneal arthrodesis into a patient having a tibia, a talus and a calcaneus bone, wherein the bone nail comprises,
- a front part configured for insertion into a bone and having a tip,
- a rear part having an end,
- wherein the rear part has a length of at least 120 mm starting from the end, wherein the bone nail is curved along a plane,
- wherein the curvature for each infinitesimal section of the bone nail on a length of at least 120 mm includes a radius of curvature which lies in a range from 130 mm to 240 mm, and
- wherein the bone nail has the same radius of curvature along its entire length along said plane, and
- wherein the method comprises fixing the tibia, talus and calcaneus bone with respect to each other by means of the bone nail.

25. The method according to claim 24, wherein the radius of curvature amounts to not more than 210 mm.

26. The method according to claim 24, wherein the radius of curvature amounts to at least 190 mm.

* * * * *